United States Patent [19]

Trerice

[11] Patent Number: 4,705,409
[45] Date of Patent: Nov. 10, 1987

[54] METHOD AND APPARATUS FOR MEASUREMENT OF CARBON CONTENT IN FLY ASH

[76] Inventor: Douglas N. Trerice, 661 Surfside Dr., Pittsburgh, Pa. 15239

[21] Appl. No.: 903,660

[22] Filed: Sep. 5, 1986

Related U.S. Application Data

[62] Division of Ser. No. 714,529, Mar. 21, 1985, Pat. No. 4,663,507.

[51] Int. Cl.$^4$ ............................................. G01N 25/00
[52] U.S. Cl. .................................. 374/45; 219/10.55 R; 219/10.55 M; 106/DIG. 1; 374/122
[58] Field of Search ................ 219/10.55 R, 10.55 M; 374/45, 10, 11, 121, 122; 106/100, DIG. 1

[56] References Cited

U.S. PATENT DOCUMENTS

| | | | |
|---|---|---|---|
| 3,277,580 | 10/1966 | Tooby | 34/1 |
| 3,449,213 | 8/1968 | Knapp | 219/10.55 |
| 3,549,848 | 12/1970 | Williams | 219/10.55 |
| 3,848,106 | 11/1974 | Berggren et al. | 219/10.55 |
| 4,071,369 | 1/1978 | Kurz et al. | 106/40 R |
| 4,121,945 | 10/1978 | Hurst | 106/DIG. 1 |
| 4,259,560 | 3/1981 | Rhodes | 219/10.55 M |
| 4,280,033 | 7/1981 | Wagener | 219/10.55 A |
| 4,282,066 | 8/1981 | Wagener et al. | 201/6 |
| 4,310,747 | 1/1982 | Rice et al. | 219/381 |
| 4,400,604 | 8/1983 | Ohtsuka et al. | 219/10.55 M |
| 4,435,374 | 3/1984 | Helm | 423/415 A |
| 4,459,450 | 7/1984 | Tyler | 219/10.55 A |
| 4,549,053 | 10/1985 | Haugh | 219/10.55 M |
| 4,565,669 | 1/1986 | Collins et al. | 422/78 |
| 4,567,340 | 1/1986 | Latchum | 219/10.55 M |

Primary Examiner—A. D. Pellinen
Assistant Examiner—Leon K. Fuller
Attorney, Agent, or Firm—Arnold B. Silverman

[57] ABSTRACT

A method and apparatus is provided for reducing and measuring carbon content in fly ash. The invention employs microwave energy as the method of heating for inducing combustion of the carbon in a fly ash sample. Measurement of the carbon content can be accomplished in accordance with the present invention by measuring temperature differential of an excess energy absorber in the form of water before and after the fly ash is exposed to microwave radiation.

4 Claims, 6 Drawing Figures

METHOD AND APPARATUS FOR MEASUREMENT OF CARBON CONTENT IN FLY ASH

This is a division of application Ser. No. 06/714,529, filed Mar. 21, 1985, now U.S. Pat. No. 4,663,507, issued Mar. 5, 1987.

BACKGROUND OF THE INVENTION

1. Field of the Invention.

This invention relates to the measurement and reduction of carbon in fly ash by employing microwave energy.

2. Description of the Prior Art.

Microwave energy has been used in various ways in the coal processing environment. For example, U.S. Pat. No. 4,259,560 to Rhodes discloses a process for drying coal and other conductive materials using microwaves. The process involves drying coal particles as they fall freely in a chamber past a microwave source.

U.S. Pat. No. 4,282,066 to Wagener, et al. discloses a process and apparatus for coking coal using microwave radiation. After the coke is created, Wagener teaches the use of photocells to cool the coke by absorbing radiation therefrom.

U.S. Pat. No. 4,435,374 to Helm, Jr., discloses a method of producing carbon monoxide and hydrogen by gasification of solid carbonaceous material. This method involves the use of microwave irradiation to convert all types of coal to carbon monoxide and hydrogen. This process involves treating the solid carbonaceous material with steam.

None of the aforementioned methods are used to reduce and measure carbon in fly ash. Known methods for measuring and reducing carbon content in fly ash do not involve microwave radiation. Furthermore, present methods of collecting a sample of ash are cumbersome and manpower intensive. Normally, a sample is collected in a combustion byproducts duct that connects a combustion zone to a particulate collection and combustion gas purification zone. The sample is a very small fraction of the total amount of material in the duct at any point in time. Because the sample is only a small fraction of the amount actually produced in the combustion zone, a small inaccuracy in the sample results in a large miscalculation of actual conditions.

There remains a need for a method and apparatus for reducing the carbon content in fly ash and for an apparatus and method of measuring the amount of carbon in fly ash. This need also remains because much of the fly ash produced by the utility industry today contains unburned carbon. This unburned carbon represents a significant loss in energy efficiency and contributes to higher electricity generation costs. Fuel must be purchased to offset the carbon in the ash. Specifically, excess air is provided to consume the carbon in the fuel. The air that is provided to combust the unburned carbon is heated by additional fuel. As this additional air removes heat energy from the combustion process and is wasted, the combustion process has a lower efficiency than could be achieved had all of the carbon in the fuel been consumed.

There are also disposal cost increases because the unburned carbon represents greater bulk. Further, carbon in ash is detrimental to utilization of ash as a cement displacement material. Thus, a significant cost reduction would be realized if carbon in ash could be reduced more efficiently.

There remains, therefore, a real and substantial need for improved means for measurement and reduction of carbon in fly ash.

SUMMARY OF THE INVENTION

The present invention has produced a solution to the need described hereinbefore by providing a process and apparatus which effectively reduces carbon in ash and provides a method for measuring the amount of carbon in ash. The measurement method and apparatus will shorten the sampling and analysis time and will increase the accuracy of present sampling and analysis methods.

The apparatus preferably has a chamber which receives fly ash. This chamber contains a porous ceramic media. A microwave input source directs microwave radiation into the chamber. There, carbon in the fly ash is heated by absorption of microwave energy. When the carbon reaches its ignition temperature of approximately 480° C. (900° F.), it begins to burn. Carbon is heated at a faster rate than other components in the fly ash and this large relative heating rate leads to the cracking and melting of ash particles containing carbon and other carbonaceous material. Combustion products escape through a flume and the remaining fly ash has a reduced carbon content.

There is further provided an excess energy absorber in the form of a water wall. Alternatively, an electronic device that is sensitive to the microwave frequency, or other suitable means, can be installed instead of the water wall to measure unabsorbed microwave energy. The measuring devices are discussed more fully hereinafter.

An object of the present invention is to provide a real time method and apparatus for reducing and measuring carbon content in fly ash, through use of microwaves.

It is a further object of the invention to permit any coal combustor to exercise greater control over combustion conditions.

It is yet a further object of the invention to increase combustion efficiency.

It is yet a further object of the invention to decrease disposal costs.

It is yet a further object of the invention to increase revenues from ash sales.

These and other objects of the invention will be fully understood from the following description of the invention with reference to the illustrations appended hereto.

DESCRIPTION OF THE PREFERRED EMBODIMENTS

The present invention provides a method and apparatus for reducing carbon in fly ash and also provides a method and apparatus for measuring the amount of carbon in fly ash.

In general, ash particles are chemically and physically similar to typical glasses. Non-polar structures such as glass are invisible to microwave radiation. An example of this are containers sold under the trademark "PYREX" which are used to hold food in homestyle microwave ovens. Glass containers absorb very little radiation because of their highly balanced chemical structure. Carbon, on the other hand is receptive to microwave radiation and absorbs microwave energy. Dr. P. D. Zavitsanos of General Electric, discusses the technical aspects of microwave absorption in his report on "Coal Desulfurization Using Microwave Energy." EPA 600/7-78-089, June 1978. That study describes a method for removing pyritic and organic sulfur from several United States coals. The method employs microwave energy to remove 50% of the pyritic sulfur and uses microwaves in combination with sodium hydroxide to remove more than 95% of the pyritic sulfur and approximately 60% of the organic sulfur. This study does not relate to fly ash or carbon reduction, but it does show that coal will absorb microwave radiation and that coal is receptive to 2,450 MHz frequency microwaves.

Measurement of carbon content can be accomplished by two methods:

(a) The excess energy absorber, energy producer, and mass throughput device may be coupled with a microprocessor. By knowing the throughput rate and the amount of energy absorbed by the fly ash (difference between input energy and excess energy collected by absorber) the microprocessor can calculate the carbon content of the ash; or (b) The other method consists of temperature rise measurements for the ash and combustion air, and comparing these measurements to the throughput rate, excess energy, and input energy.

The first method is preferable below the ignition point for the carbon, but it can also be used when carbon is being combusted. Microwave energy that is absorbed by the carbon is lost to the chamber as heat. By comparing microwave energy input to unabsorbed energy one can calculate the amount of carbon entering the chamber. The second method is a total energy balance method of determining carbon content. Fly ash and air input temperatures and mass flow rates are measured and compared to output temperatures and rates. Microwave energy input and output (excess) are also measured. If carbon is combusting it provides additional energy to the system (heat of combustion). By knowing the system temperature rise, the amount of microwave energy absorbed and the amount of carbon that is oxidized, one can calculate the amount of carbon that entered the system.

The second method can be used above and below the carbon ignition point. The first method assumes that absorbed microwave energy is directly proportional to carbon content of the ash. The second method incorporates this first assumption as well as an oxidation assumption. In one embodiment of the invention, another microwave input and output device may be added to measure resulting carbon oxidation in the first unit. This system, consisting of two units, does not require full carbon burnout in the first chamber to facilitate carbon measurement. An energy balance (input minus output) would be performed on both units. The combination of these two balances is directly proportional to the carbon content of the ash entering the first unit. The second microwave chamber can be used to control the throughput in the first chamber. If carbon is perceived in the second chamber then flow rate of ash will be reduced so that complete carbon combustion can take place in the first unit.

Figure 4:
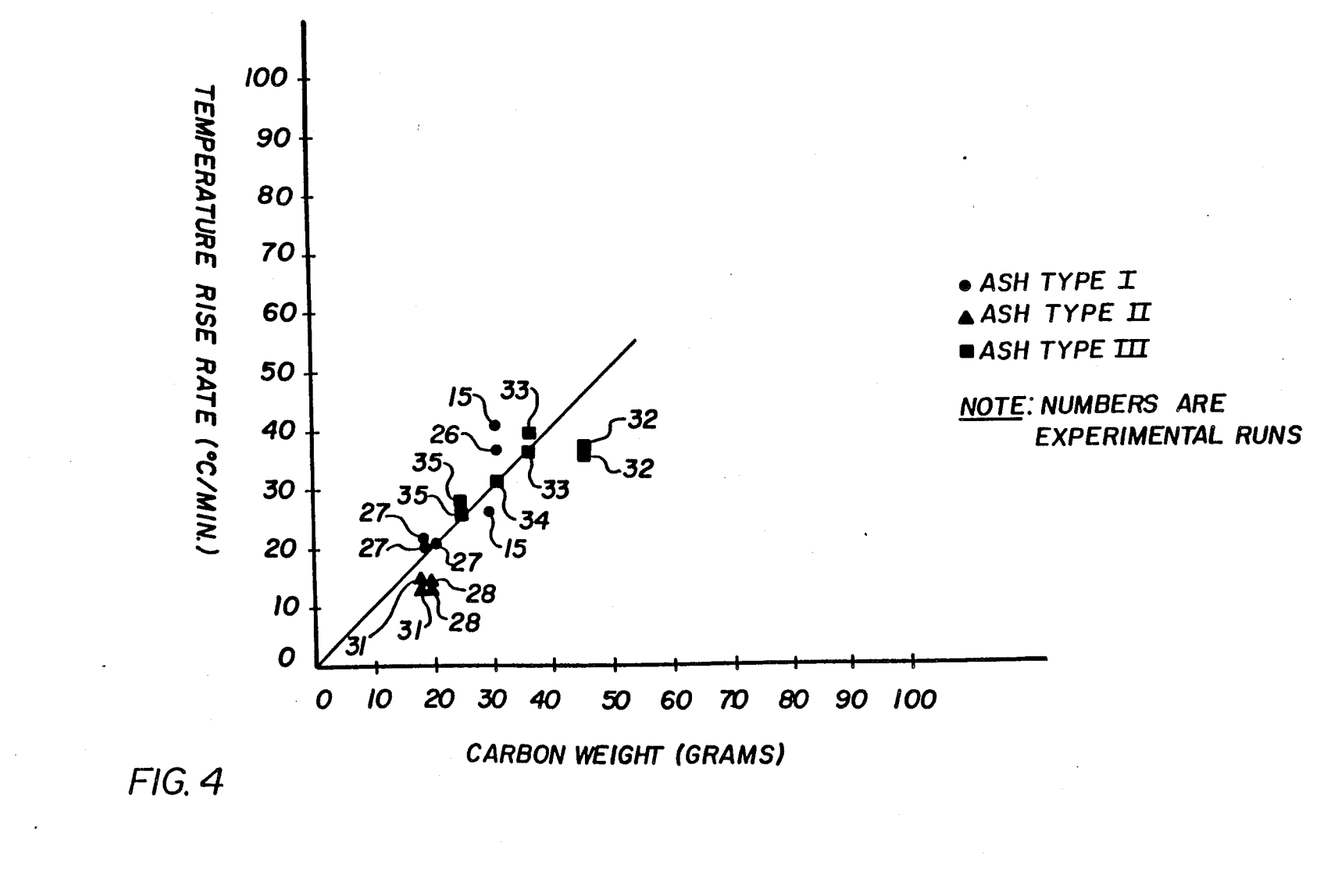
FIG. 4 a graph showing fly ash temperature rise rate as a function of carbon concentration in the ash.

FIG. 4 shows fly ash temperature rise rate as a function of carbon concentration in the ash. The experimental results teach us that temperature rises faster with higher carbon content ashes than with lower carbon content ashes. By measuring the temperature rise rate, the carbon content of the ash can be determined. Because the temperature rise rate is directly proportional to the quantity of microwave energy absorbed by the carbon, carbon content can also be ascertained by measuring the amount of microwave energy that is absorbed by the fly ash. This may be measured with the water wall, which captures excess energy that was not absorbed by the carbon. The water wall energy is subtracted from the amount of microwave energy entering the chamber to arrive at the quantity absorbed by the carbon.

More specifically, the energy absorbed in fly ash when it is heated, either by microwaves or another heat source, can be calculated with the following equation:

$$MVe = (Cw \times CSpH \times (T_2 - T_1)) + (FAGw \times FAGSpH \times (T_2 - T_1))$$

where $MVe$ = Energy Absorbed
$Cw$ = Carbon Weight
$CSpH$ = Carbon Specific Heat (Heat Capacity)
$T_2 - T_1$ = Temperature Change
$FAGw$ = Fly Ash Glass Weight
$FAGSpH$ = Fly Ash Glass Specific Heat
$FAw$ = Fly Ash Weight = $FAGw + Cw$ Fly ash glass consists of many components that have fused together. It contains alumina, silica, iron oxides, alkaline earths, and other species that were contained in the coal and were not consumed in the combustion process. Some of these complex species may absorb microwave energy as well. For a particular ash, the measurement and reduction unit can be calibrated to take into account any absorption by other than carbon components.

In effect, $FAG_w$ is placed in the equation to account for microwave absorption by other species (in the aggregate) that may also be susceptible to the microwave frequency. After the unit is calibrated on a particular ash, the right hand side of the equation becomes a calibration constant and will only need to be changed if a new ash of different chemical analysis is to be combusted.

Figure 6:
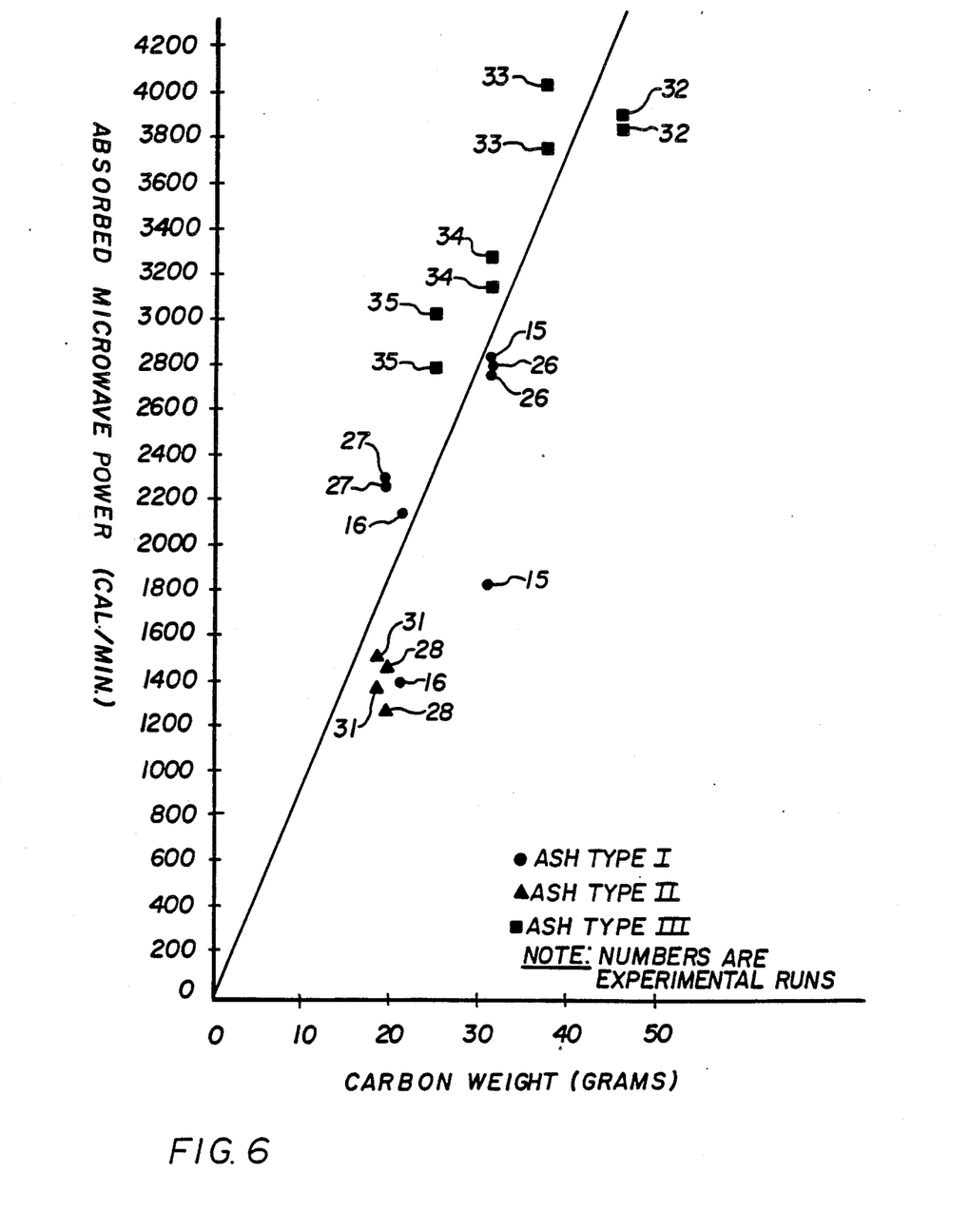
FIG. 6 is a graph showing microwave absorption by carbon.

For example, FIG. 6 shows the results of experimentation. The quantity of microwave energy absorbed is shown to be directly proportional to the ash carbon content. For the reactor under study the following equation represents this relationship:

$$MVe = 95.0 \times Cw$$

where

MVe = Microwave energy absorbed by ash
Cw = Weight of carbon in ash

Assuming that the two components, carbon and glass are closely associated, then absorbed energy can transfer by conduction from one species to the other. Although fly ash is a good insulator, temperature equilibrium will occur given sufficient time. The above equation can be rearranged as follows:

$$MVe/(T_2-T_1) = (Cw \times CSpH) + (FAGw \times FAGSpH)$$

and $$MVe/((T_2-T_1) \times Cw) = CSpH + (FAGw/Cw) \times FAGSpH \qquad (1)$$

Figure 5:
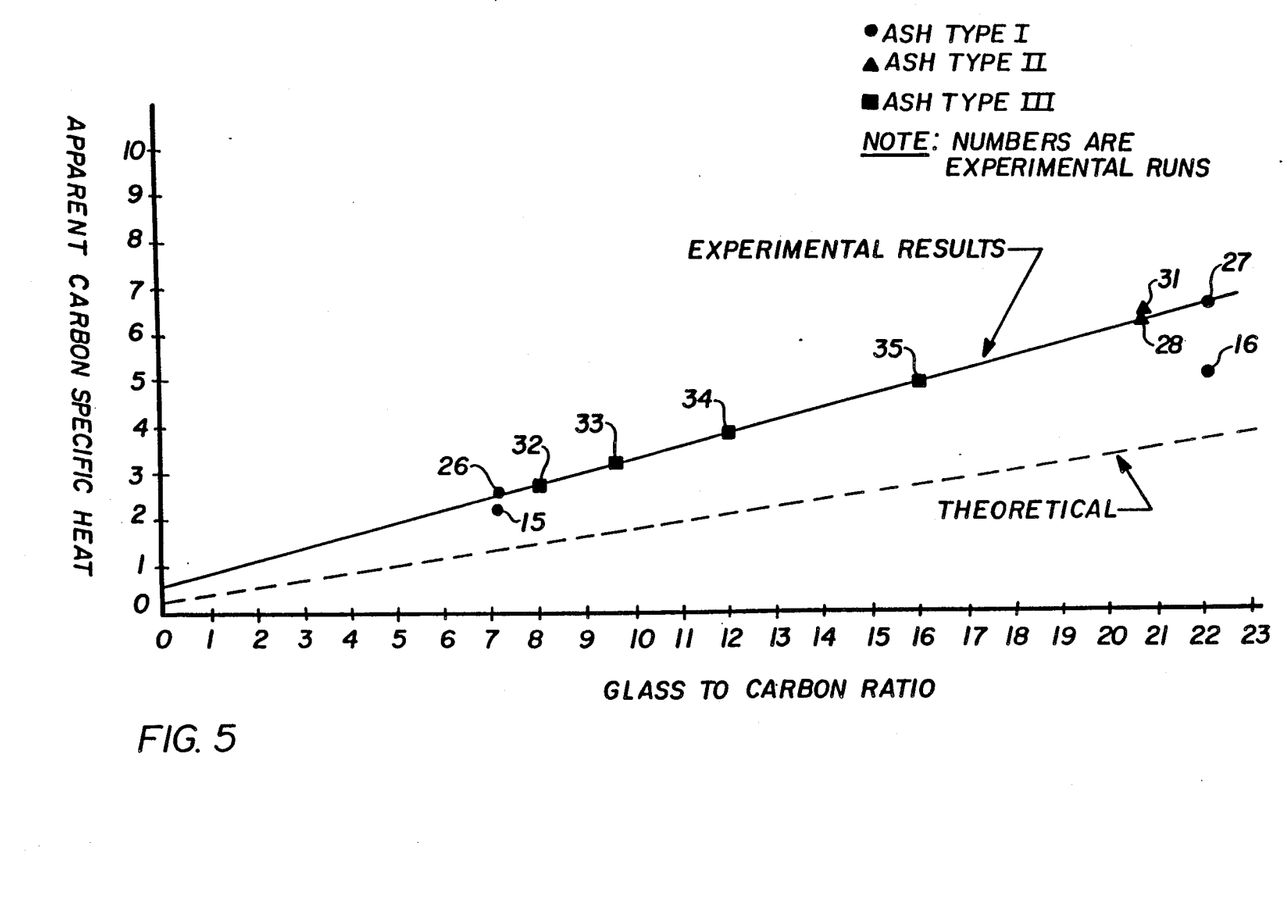
FIG. 5 is a graph showing apparent carbon specific heat as a function of carbon content.

Because CSpH and FAGSpH are nearly constant, then a plot of $MVe/((T_2-T_1) \times Cw)$ and $(FAGw/Cw)$ should be a straight line. This linear relation has been shown to exist using the method of the present invention. See FIG. 5.

The experimental results had a steeper slope and higher intercept when compared to the theoretical relationship. The theoretical and experimental equations are as follows:

Experimental Results $$MVe/((T_2-T_1) \times Cw) = 0.599 + 0.266(FAGW/Cw) \qquad (2)$$

Theoretical Results $$MVe/((T_2-T_1) \times Cw) = 0.240 + 0.150(FAGW/Cw) \qquad (3)$$

If we hold FAGw and Cw constant at 399.8 and 24.90, respectively, a comparison of actual to theoretical is as follows:

Experimental Results $$MVe/(T_2-T_1) = 121.3 \qquad (4)$$

Theoretical Results $$MVe/(T_2-T_1) = 65.9 \qquad (5)$$

Nothing was done with the experimental conditions to change the theoretical specific heat for carbon or for fly ash. These results show that microwaved fly ash evolves more heat than theoretically possible.

When carbon reaches its ignition temperature of approximately 480° C. (900° F.), it burns in the presence of oxygen to form carbon dioxide and heat energy in the amount of 7831 calorie per gram (14,087 Btu/lb.). In the microwave process, the carbon reaches its oxidation temperature, independently of the rest of the ash. In a conventional heating system whereby heat is principally absorbed by conduction, both the carbon and ash are heated simultaneously and absorb applied energy simultaneously. In both cases, carbon begins to oxidize and supplies combustion energy to the system. This heat is absorbed by the ash to some extent or leaves the system as hot gas in both types of systems (microwaved or conventional).

The experimental results show a decrease in efficiency over that obtained with ideal conventional heating methods. Using equation (4) and (5) for a temperature rise of 450° C., which represents heating an ash sample from ambient temperature to the carbon ignition point, the experimental results show that 54,600 cal are required but theoretical requirements are only 26,600 cal. The experimental apparatus was not insulated and the difference in requirements is due to heat losses. What is important is the fact that the carbon absorbs the majority of the microwaves and produces the fly ash temperature rise.

To demonstrate the potential efficiency of a microwave based carbon reduction process, equation (1) can be used as the basis.

The energy required to heat carbon to its ignition point in an ideal conventional process is as follows:

$$Q = (0.24 \times C_w \times 450) + (0.15 \times FAG_w \times 450) \qquad (a)$$

The energy required to heat carbon to its ignition point in a microwave reactor is as follows:

$$MVe = 0.24 \times C_w \times 450 \text{ (only carbon is heated by microwaves)} \qquad (b)$$

If both reactors contain the same amount of ash and both ashes contain the same amount of carbon, then a direct comparison of energy requirements can be made.

An example is as follows for $C_w = 5.0$ and $FAG_w = 95$, which represents a 5% carbon concentration.

$$Q = (0.24 \times 5.0 \times 450) + (0.15 \times 95.0 \times 450)$$
$$= 695.25$$
$$MVe = 0.24 \times 5.0 \times 450$$
$$= 540.0$$

The above example demonstrates that the amount of energy required to raise carbon to its ignition temperature is much lower in the case of microwave absorption, because the carbon is selectively heated by the microwaves and the fly ash glass absorbs little microwave energy if any at all.

Because carbon in the ash will transfer some of its heat to the ash, the temperature of the ash will also rise and the above ideal relationship is not possible in practice (Equation b). The experimental work did not compare conventional heating to microwave heating but concentrated on carbon measurement. An actual comparison of efficiency is not available. It stands to reason, however, that because microwave energy is being selectively absorbed by carbon and because the remaining ash is a poor heat conductor, then the carbon temperature will rise faster than the remaining ash. The carbon only needs to reach its ignition temperature to provide additional heat to the process. Some of this heat will be absorbed by the fly ash and the rest will leave the system in the combustion gases.

Measurements indicate that carbon was lost during microwave experiments although final temperature of the ash was only 278° C. (ignition point is 480° C.).

Under conventional conditions with an ideal reactor (no heat loss) Equation (3) is applicable. For this particular experimental run, the conventional heating requirements would be as follows:

$$Q = 0.240 \times 37.01 \times (480.0 - 21.0) + 0.150 \times 613.49 \times$$
$$(480.0 - 21.0)$$
$$= 4077.0 + 42,239.0$$
$$= 46,316 \text{ cal}$$

Microwave energy absorbed by the same ash under the same conditions was as follows:

$$MVe = 0.24 \times 37.01 \times (278.0 - 21.0) + 0.15 \times 613.49 \times$$
$$(278.0 - 21.0)$$
$$= 2,283 + 23,650$$
$$= 25,933 \text{ cal}$$

The experimental results show that microwave induced reduction of carbon requires only 56% of the energy required by conventional means, under the same heat loss conditions.

The results obtained in accordance with the present invention support the theory that carbon absorbs the microwave energy to a greater extent than the other substances in the fly ash. This being the case, microwaving is a more efficient method of oxidizing carbon in fly ash than conventional heating methods.

Given the above conclusions and experimental results, the carbon content of fly ash can also be measured, using microwaves. According to Equation (1) $[MVe=(Cw \times CSpH \times (T_2-T_1))+(FAGw-\times FAGSpH \times (T_2-T_1))]$. Temperature rise of the fly ash is a function of energy absorbed, carbon content, fly ash weight, and the specific heat of carbon and fly ash. Since specific heats are constant (or can be classified for various temperatures) absorbed energy and temperature rise are equatable. Since microwaves are absorbed by the carbon, the temperature rise will result from the quantity of carbon in the fly ash and carbon absorption coefficient. Temperature rise or energy absorbed will be directly proportional to carbon content.

Figure 1:
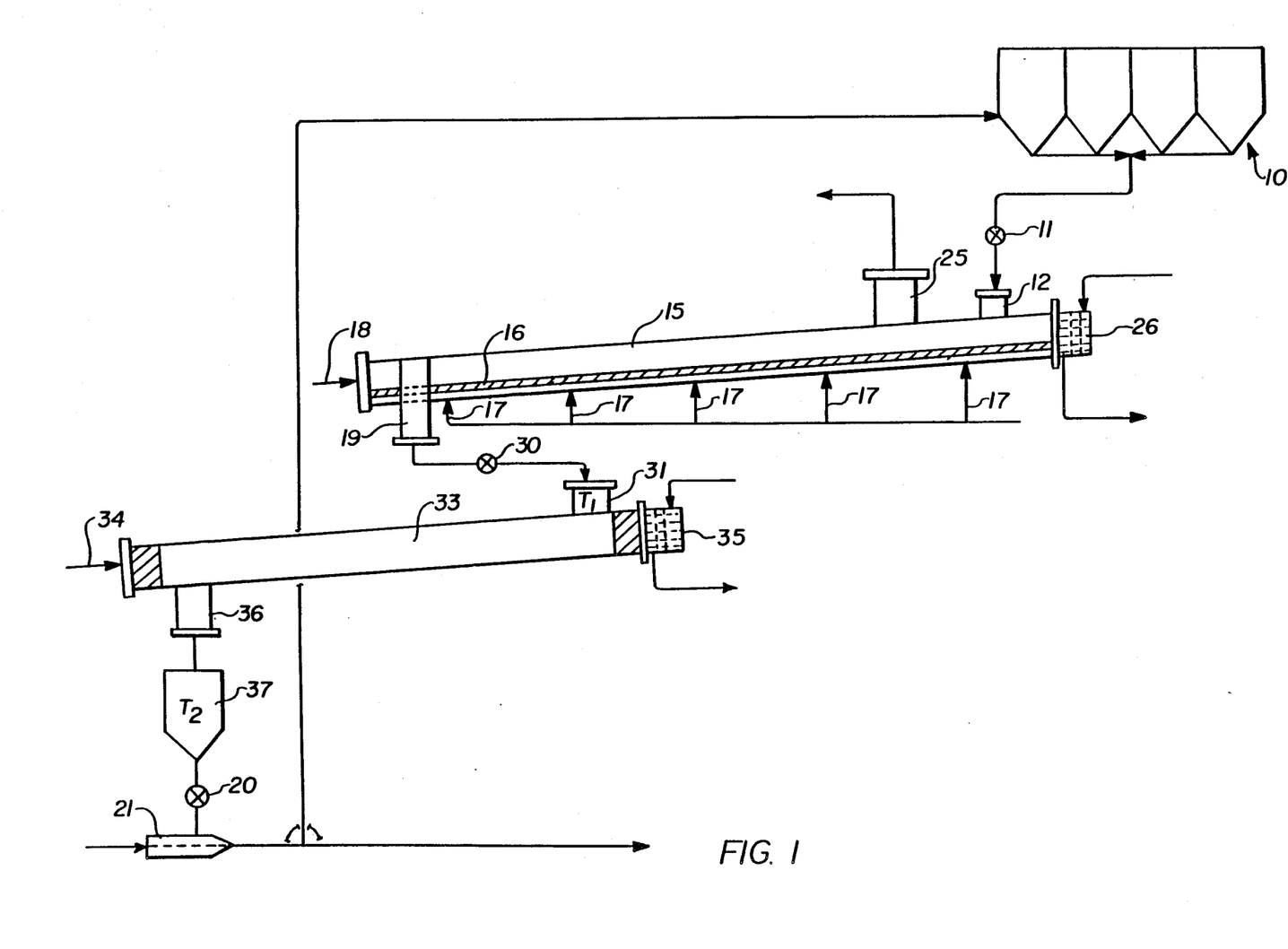
FIG. 1 is a schematic illustration of one embodiment of the device of the present invention showing the fly ash reactor in connection with the measuring device of the present invention.

Referring now to FIG. 1 which is a schematic of the fly ash reactor in combination with the measurement device of the present invention, fly ash from any suitable source, such as the residue discharge from electrostatic precipitators 10, is fed through a flow control valve 11, and through inlet conduit 12. The feed enters on energy absortion chamber 15 within which there is porous ceramic media 16. This media is preferably comprised of sintered glass or conventional ceramic material. The rectangular chamber receives low pressure air as depicted by arrows 17, the air pressure would be preferably 25 inches water gage. The fly ash is heated by microwave radiation which is directed through chamber 15 from any suitable microwave source depicted by arrow 18. The carbon in the fly ash is heated by microwaves in the presence of air and until the combustion temperature of the carbon is reached. The carbon is oxidized and the combustion products go off through flume 25 to a suitable heat recovery unit. The microwaved ash which remains, is discharged through outlet conduit 19.

For measuring the amount of carbon in the fly ash, the ash from discharge 19 enters inlet conduit 31 through control valve 30 from a source such as electrostatic precipitators 10. Temperature is monitored by thermo couple or other suitable measuring device as shown at $T_1$. The ash thereafter enters absorption chamber 33. Microwave radiation is directed into absorption chamber 33 through a microwave input source depicted by arrow 34. Within the chamber 33, the ash is exposed to microwave energy at a frequency of preferably about 2200 to 2500 $MH_z$. Thereafter the microwaved ash passes through conduit 36 into equilibrium chamber 37 where the new temperature $T_2$ is monitored. Excess energy absorber 35 is shown and may be in the form of a water wall.

Rotary valve 20 controls the flow of ash to airveyor 21 which transports the microwaved ash to a storage silo or back to the source. Water wall 26 acts as an excess energy absorber to absorb microwave energy and provides a second means for measuring ash carbon content.

Figure 2:
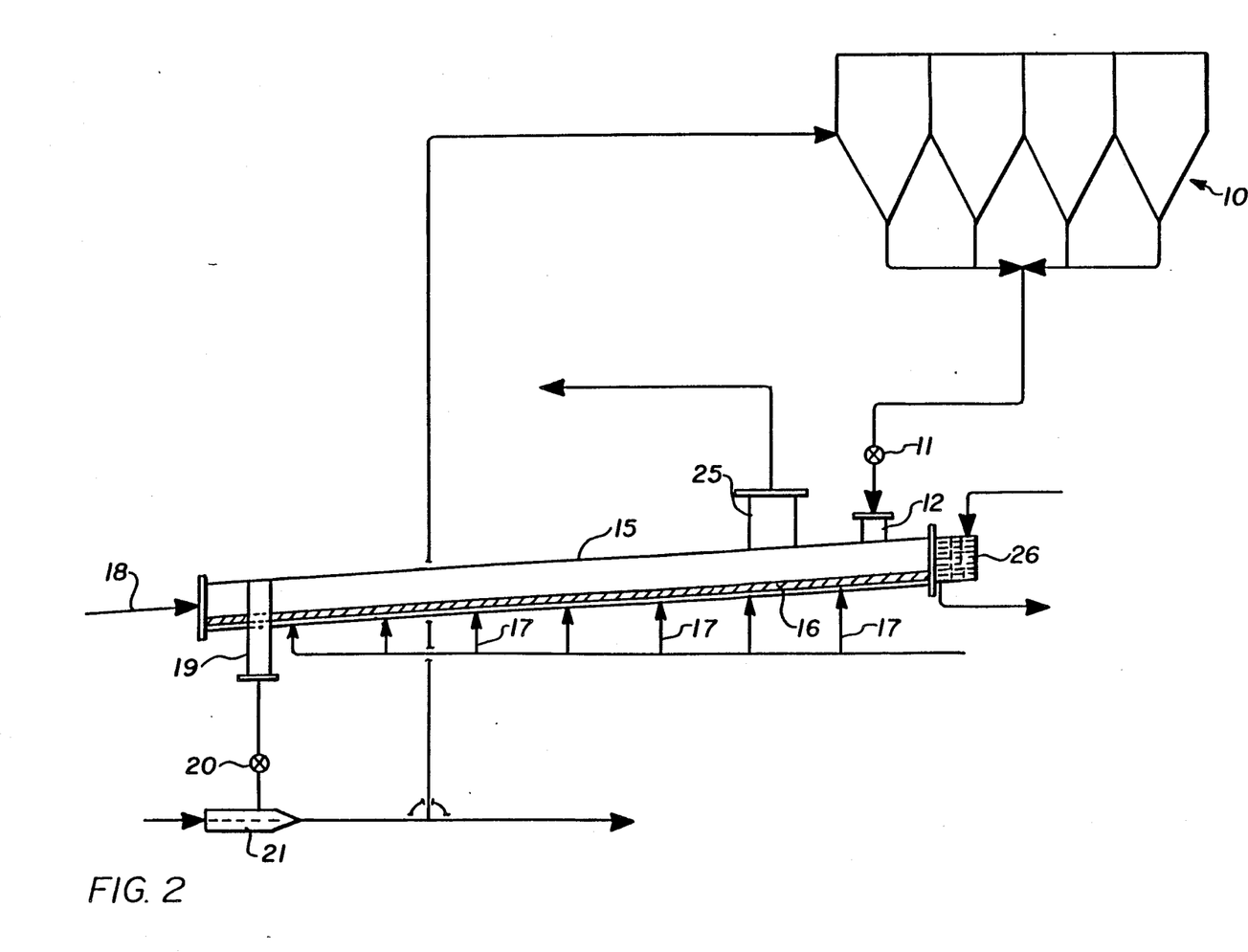
FIG. 2 is a schematic illustration of one embodiment of the fly ash reactor of the present invention used to reduce carbon content in the ash.
Figure 3:
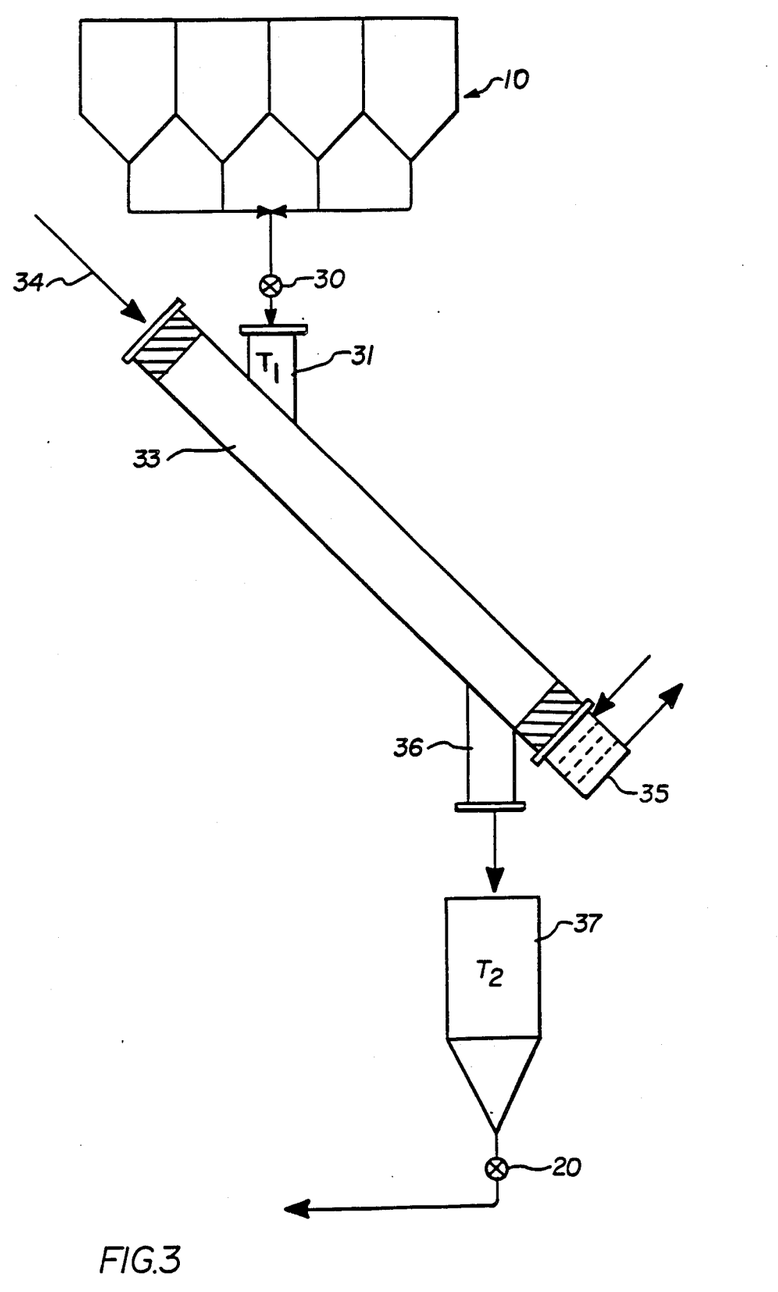
FIG. 3 is a schematic illustration of one embodiment of the fly ash measurement device of the present invention.

See also FIGS. 2 and 3 which show, respectively, the reactor and another embodiment of the measuring device.

It will be appreciated that the present invention has provided an effective method and apparatus for reducing and measuring carbon content in fly ash. By using microwaves, in accordance with the present invention, this can be accomplished efficiently and at lower energy costs.

Whereas particular embodiments of the invention have been described above for purposes of illustration, it would be evident to those skilled in the art that numerous variations of the details may be made without departing from the invention as defined in the appended claims.

I claim:

1. A method of measuring the amount of carbon in fly ash comprising,
   exposing the fly ash to microwave radiation,
   absorbing excess energy not absorbed by the fly ash in an absorption fluid, and
   measuring the temperature differential of said fluid before and after microwave absorption.

2. The method as set forth in claim 1 wherein said absorption fluid is water.

3. An apparatus for measuring carbon content in fly ash comprising,
   an absorption chamber having an inlet conduit and an outlet conduit, said inlet conduit having a flow control valve and temperature monitoring means operatively associated therewith,
   microwave generating means for introducing microwave energy into said absorption chamber, and
   an equilibrium chamber operatively associated with said outlet conduit, said equilibrium chamber having temperature monitoring means for measuring the temperature after absorption.

4. The apparatus of claim 3 wherein said absorption chamber is elongated and generally rectangular.

* * * * *